(12) United States Patent
Schwartz et al.

(10) Patent No.: US 6,967,103 B2
(45) Date of Patent: Nov. 22, 2005

(54) APPARATUS AND METHODS FOR DETECTING EXPLOSIVES AND OTHER SUBSTANCES

(75) Inventors: Paul D. Schwartz, Arnold, MD (US); George M. Murray, Columbia, MD (US); O. Manuel Uy, Ellicott City, MD (US); Binh Q. Le, Vienna, VA (US); David D. Scott, Columbia, MD (US); Ark L. Lew, Ellicott City, MD (US); Sharon X. Ling, Clarksville, MD (US); Joseph J. Suter, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 220 days.

(21) Appl. No.: 10/240,902

(22) PCT Filed: May 3, 2001

(86) PCT No.: PCT/US01/14190

§ 371 (c)(1),
(2), (4) Date: Jan. 21, 2003

(87) PCT Pub. No.: WO01/86263

PCT Pub. Date: Nov. 15, 2001

(65) Prior Publication Data

US 2003/0143119 A1    Jul. 31, 2003

Related U.S. Application Data

(60) Provisional application No. 60/201,856, filed on May 4, 2000.

(51) Int. Cl.$^7$ ............................................. G01N 21/64
(52) U.S. Cl. ..................... 436/106; 436/107; 436/110; 436/111; 436/156; 436/172
(58) Field of Search .......................... 422/82.05, 82.07, 422/82.08, 82.11; 436/436, 156, 106, 107, 436/110, 111, 172; 250/458.1, 459.1

(56) References Cited

U.S. PATENT DOCUMENTS

| | | | | |
|---|---|---|---|---|
| 5,157,261 A | * | 10/1992 | Grey et al. | 250/458.1 |
| 5,166,990 A | * | 11/1992 | Riccitelli et al. | 385/12 |
| 5,638,166 A | * | 6/1997 | Funsten et al. | 356/36 |
| 6,749,811 B2 | * | 6/2004 | Murray | 422/91 |

FOREIGN PATENT DOCUMENTS

WO    WO 99/57222    * 11/1999

OTHER PUBLICATIONS

Kriz, D. et al, "Introducing Biomimetic Sensors Based on Molecularly Imprinted Polymers as Recognition Elements" Anal. Chem. 1995, vol. 67, pp. 2142-2144.*

(Continued)

*Primary Examiner*—Jeffrey R. Snay
(74) *Attorney, Agent, or Firm*—Francis A. Cooch

(57) ABSTRACT

An explosive detector that utilizes an array of molecularly imprinted polymer (MIP) coated, bifurcated fiber optic cables to form an image of a target molecule source. Individual sensor fiber assemblies, each with a calibrated airflow, are used to expose the fibers to the target molecule. The detector energizes a dedicated excitation light source for each fiber, while simultaneously reading and processing the intensity of the resulting fluorescence that is indicative of the concentration of the target molecule. Processing electronics precisely controls the excitation current, and measures the detected signal from each narrow band pass filter and photodiode. A computer with display processes the data to form an image of the target molecule source that can be used to identify the source even when low level contamination of the same molecule is present. The detector can be used to detect multiple and/or non-explosive targets by varying the MIP coating.

18 Claims, 2 Drawing Sheets

OTHER PUBLICATIONS

Albert, K. et al, "Designing Optical Sensor Arrays with Enhanced Sensitivity for Explosives Detection" Chemical Abstracts, 1998, Abstract No. 130:97710.*

Arnold, B. et al, "Progress in the Development of Molecularly Imprinted Polymer Sensors" Johns Hopkins APL Technical Digest, 1999, vol. 20, No. 2, pp. 190-198.*

* cited by examiner

APPARATUS AND METHODS FOR DETECTING EXPLOSIVES AND OTHER SUBSTANCES

CROSS-REFERENCE TO RELATED APPLICATIONS

This application claims the benefit of prior filed, now abandoned U.S. provisional application Ser. No. 60/201,856, filed on May 4, 2000.

BACKGROUND OF THE INVENTION

1. Field of the Invention

The invention relates generally to electromechanical devices for detecting explosives and other substances and, more specifically, is a battery powered, stand-alone, portable detector that utilizes molecularly imprinted polymer coated fiber optic cables to form an image of a target molecule source that can be used to identify the source.

2. Description of the Related Art

With an estimated 100 million mines and countless millions of acres of land contaminated with unexploded ordnance (UXO) worldwide there is a need for sensor systems and methods that can detect and identify large and small explosive objects buried in soil. In addition, during armed conflict, there is a need for mine detection and neutralization in real-time or near real-time.

A commonly used sensor for mine and UXO detection is the electromagnetic induction (EMI) metal detector. Conventional EMI metal detectors using either frequency-domain (FD) or time-domain (TD) eddy current methods can detect small metal targets (such as plastic-cased low-metal content mines) at shallow depths and large metal targets (such as metal-cased high-metal content mines and UXOs) at both shallow and deep depths under a wide range of environmental and soil conditions. However, metal non-mine (i.e., clutter) objects commonly found in the environment pose a major problem in identifying mines. That is because these clutter objects create false alarms when detected by a metal detector. For time-efficient and cost-effective land clearing, the detected metal targets must be classified as to their threat potential: mine, UXO or clutter. Preferably, these metal targets need to be classified in real-time or near real-time.

Other explosive detection methods utilize neutron beams and energy detection to characterize the organic compounds under surveillance. Although these devices may be effective, they are too massive, non-portable, and, because of the neutron and gamma radiation, cannot be used near humans without effective shielding, i.e., lead, water or polyethylene.

Dogs can also be trained to sniff out explosives, but the drawbacks are that they require a trainer/handler and have a limited attention span.

Remote chemical sensors can be used to detect explosives but must fulfill two goals: (1) the development of a specific chemical recognition element that allows a molecule, or class of molecule, to be identified, and (2) a means of signal transduction in which the presence of the molecule causes a measurable change in a physical property of the material. Although these goals are not always separable, the successful design of chemical sensors requires that both be satisfied.

Most transduction approaches are based on optical, resistive, surface acoustic wave, or capacitive measurements. These well-developed methods dominate largely because of their ease of operation, sensitivity, and cost. The chemical recognition elements in these detectors, however, lag far behind. Indeed, most reports on chemical sensors suggest that many other devices could be fabricated if only suitable chemical recognition units were available. The missing element is a general approach to chemical recognition that allows the rational design and assembly of materials in a stable and reusable form.

Methods for the detection of explosives and explosive residues require complex analytical instruments such as liquid or gas chromatographs coupled with mass spectroscopic or chemiluminescent detection. The associated instrumentation is usually large, expensive, difficult to maintain and requires skilled operators. If laboratory analysis is necessary, extensive documentation is needed for sample transport, increasing the possibility of sample contamination. Immunoassay tests are available for some explosives, but these are cumbersome and have short shelf lives.

U.S. Pat. No. 5,157,261, issued Oct. 20, 1992, discloses a portable fiber optic detector that senses the presence of specific target chemicals by electrostatically attracting the target chemical to an aromatic compound coating on an optical fiber. Attaching the target chemical to the coated fiber reduces the fluorescence so that a photon sensing detector records the reduced light level and activates an appropriate alarm or indicator.

However, the concentration of the aromatic compound coating on the optical fiber has to be optimum or the fluorescence will be either too strong or too weak. Furthermore, if target chemicals from a neighboring exploded mine are present, the detector may become saturated and be ineffective. Additionally, the detector only sounds an alarm and does not provide an image of the explosive device being detected. The detector also does not provide the ability to detect multiple substances simultaneously.

What is needed then is a detection device for explosives or other substances that can be easily programmed for the substance(s), that can detect targets in an environment with high background levels of the target substance, that can detect multiple substances simultaneously, and that can provide an image of the substance emitting target.

SUMMARY OF THE INVENTION

The present invention provides a simple, relatively low cost, stand-alone, portable device that can be used virtually anywhere including close proximity to humans. The invention generates an image of buried land mines that aids in reducing false positives, identifying mine type, and recognizing mine orientation.

While the sensor element of the detector of the invention can take many forms, a preferred embodiment uses a molecularly imprinted polymer (MIP) which is generally described as a plastic cast or mold of the molecule of interest, where recognition is based on shape, much like a lock and key. MIPs are made by adding the molecule of interest to a solution of binding molecules that can be chemically incorporated into a polymer. These binders usually have an affinity for the target and form a complex.

The interactions that hold these complexes together include II—II interactions, hydrogen bonding, metal-ligand binding, and even covalent bond formation, but they must be reversible. The binder must also have a chemical functionality that allows it to be irreversibly bound to polymers. Vinyl groups are a common functional group used to prepare many polymers, e.g., polyethylene, polystyrene, polyvinylalcohol, and polyvinylchloride. The target-binder complex is dissolved in excess monomer (for example, styrene) and possibly other additives such as a cross-linker and porogens (solvents).

In a typical sensor fabrication, a solid plastic mass, consisting of the matrix and binder, is obtained which is chemically bound to the polymer/cross-linker matrix and the target molecule. Removal of the target is possible since it is reversibly bound to the binder. The cavity it leaves behind is permanently shaped like the target.

The explosive embodiment of the detector of the invention utilizes an array of MIP coated, bifurcated fiber optic cables to form an image of a target molecule source to detect and identify trace levels of explosive material emanating from land mines. Individual sensor fiber assemblies, each with a calibrated airflow, are used to expose the fibers to the target molecule. The detector energizes a dedicated excitation light source for each fiber, and, through a detector element, e.g., a filter and photodiode, simultaneously reads and processes the intensity of the resulting fluorescence that is indicative of the concentration of the target molecule. Processing electronics precisely control the excitation current, and measures the detected signal from each filter and photodiode.

A computer with display processes the data from each calibrated detector element to form an image of the target molecule source that can be used to identify the source even when low level contamination of the same molecule is present. The detector can be used to detect multiple targets by varying the MIP coating. Where mere detection of the presence of a target molecule is satisfactory, the array can be reduced to a single fiber assembly for each target molecule. The detector can be modified to detect other (non-explosive) materials by changing the MIP coating and selecting appropriate light sources, photodetectors, and filters.

DETAILED DESCRIPTION

While the invention will now be described in detail in the context of its use to detect explosives, it will readily be seen, as explained further, that the invention can be modified to detect other (non-explosive) substances. Furthermore, while a preferred embodiment of the invention utilizes MIP coated fiber optic cables, it will be appreciated that other sensor elements could be used as well.

Figure 2:
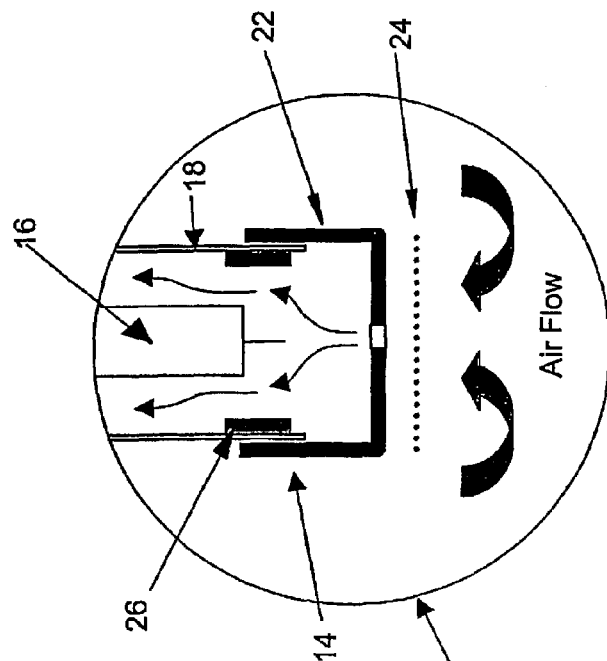
FIG. 2 is a detailed schematic view of the tip of one of the sensor fiber assemblies of the detector of the invention.
Figure 3:
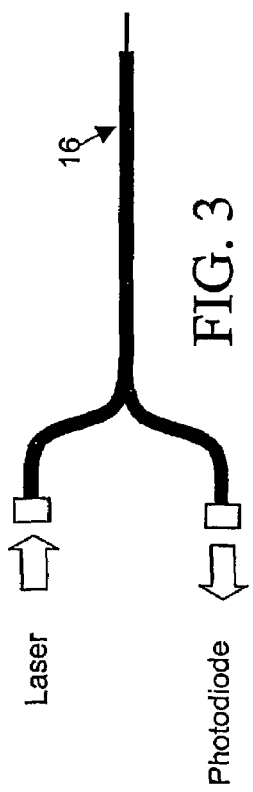
FIG. 3 illustrates the bifurcated fiber comprising the sensor fiber assembly of the detector of the invention.
Figure 1:
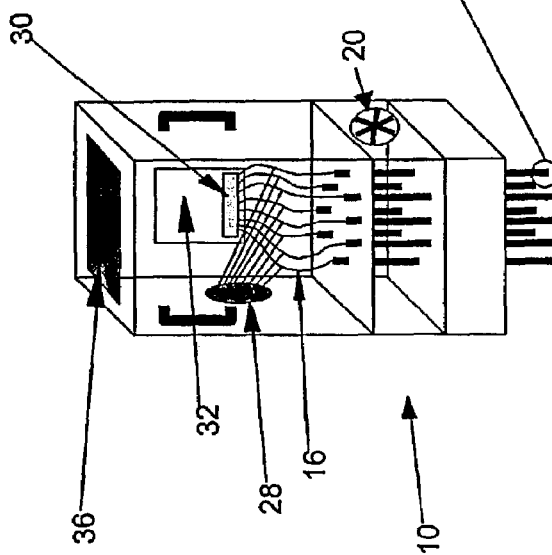
FIG. 1 is a schematic of the detector of the invention.

Turning now to FIG. 1, the invention comprises a battery powered, stand-alone detector 10 comprising, in part, one and, in many cases preferably, an array 12 of sensor fiber assemblies for sensing the presence of target molecules from one or more chemicals found in explosives. As shown in FIG. 2, each sensor fiber assembly 14 comprises a bifurcated fiber optic cable 16, as also shown in FIG. 3, for receiving light from an excitation source and simultaneously returning fluorescence to a detector.

The tip of each fiber optic cable is coated with a molecularly imprinted polymer (MIP), the MIP designed and implemented as described in U.S. patent application Ser. No. 09/300,867, filed Apr. 28, 1999, and international application, serial no. PCT/US01/11562, filed Apr. 10, 2001 (RO/US), both of which are incorporated herein by reference. In one embodiment, the MIP contains incorporated therein porphyrin moieties which selectively bind a target molecule which comprises an explosive chemical. The MIP is formed by the steps comprising:

(A) providing the reaction product of (i) a polymerizable porphyrin derivative and (ii) a target molecule comprising an explosive chemical;

(B) copolymerizing the reaction product of step (A) with monomer and crosslinking agent to form a polymer; and (C) removing the target molecule from the polymer, said polymer exhibiting selecting binding affinity for the target molecule and undergoing a detectable change in absorption and/or emission of electromagnetic radiation when the target molecule binds thereto.

The MIP coating provides a large dynamic range as the sensing element. Different MIP coatings can be used in the array either serially, or simultaneously on different sensor fiber assemblies, to detect one or multiple explosive chemicals, including the three major land mine explosives. The MIP used can also be designed to detect non-explosive substances, if desired.

In addition to the MIP coated, bifurcated fiber optic cable, each sensor fiber assembly further comprises a thermally insulated tube 18 in which the fiber optic cable is inserted. A fan array 20 is placed in the detector to draw a calibrated airflow over the coated fiber optic cable tips to expose each sensor assembly to target molecules. The fan array can be computer/microprocessor controlled to form an air evacuation system.

Also part of the sensor fiber assembly is a position adjustable nozzle 22 for adjusting airflow into the tube and over the fiber optic cable and a dust screen 24 for removing dust and other particles not of interest. At the end of each tube is a heater 26 of, e.g., one watt, which is used to heat the fiber which will then release the bound target molecules, i.e., will "clear" the sensor, so that it can be reused.

Figure 4:
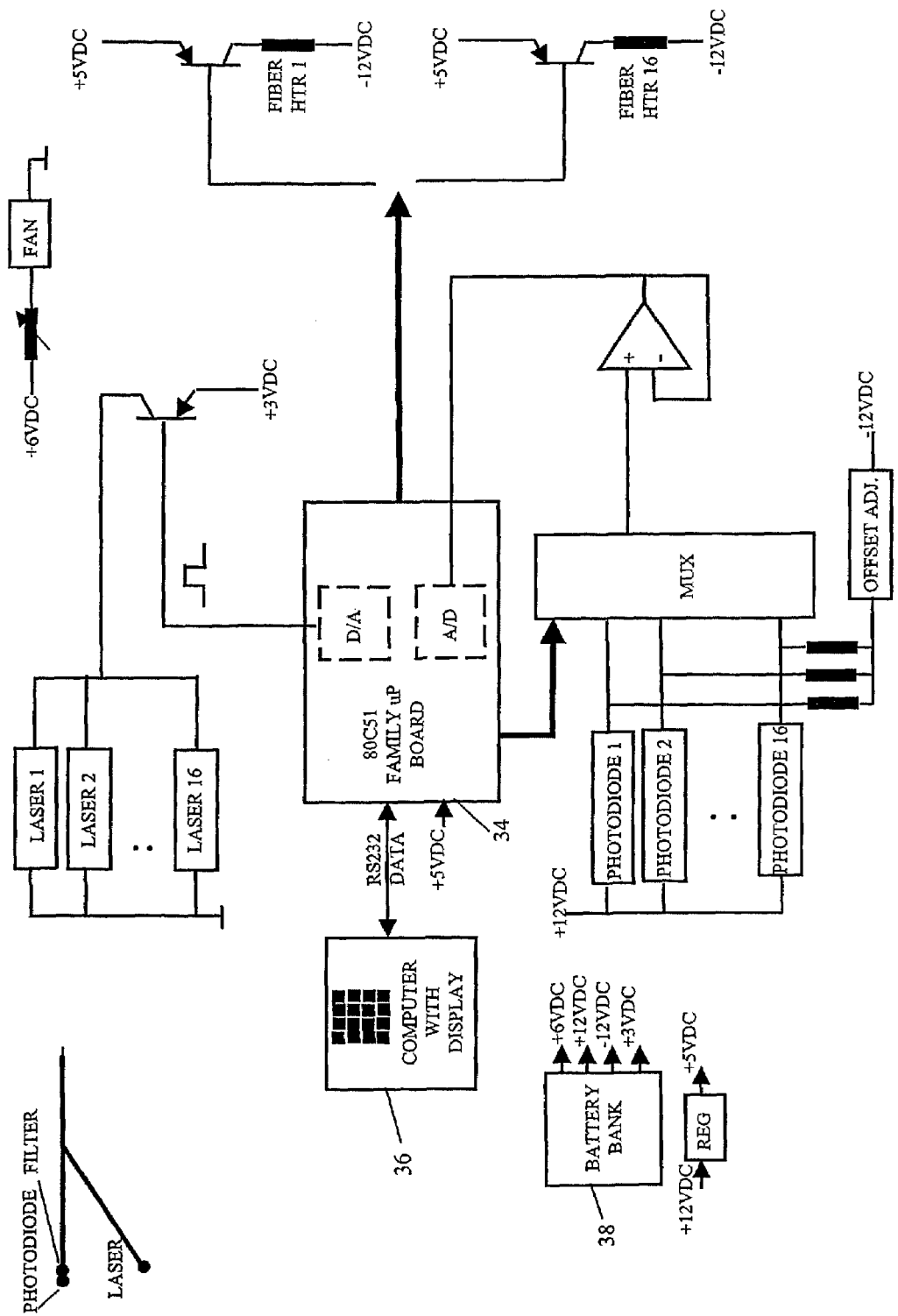
FIG. 4 is a diagram of the electronics of the detector of the invention.

Returning to FIG. 1, each sensor fiber assembly in the array is connected via the bifurcated fiber optic cable to both a dedicated excitation source 28, for example, a red (690 nm) laser, and to a dedicated detector element 30, comprising, for example, a photodiode and a narrow band pass filter. The lasers and photodiodes are connected to control electronics 32 including a microprocessor 34 (see FIG. 4 for microprocessor). The control electronics and microprocessor therein control sampling for each of the channels formed by the sensor fiber assembly, fiber optic cable, light source, and detector by precisely controlling the excitation current and measuring the detected signal from each detector element. A computer with display 36 is also provided as shown in FIGS. 3 and 4. To provide true portability the detector is powered by batteries 38.

In operation, the fan array draws air in over the MIP coated fiber optic cable tips to expose each to target molecules which if present will bind to the MIP coating. Periodically, for example, once each second, the microprocessor and control electronics energize, e.g., turn on, the excitation light source, e.g., laser, dedicated to each fiber optic cable. If target molecules are present, the light will cause them to fluoresce, the light generated from the fluorescence process traveling by means of internal reflection along the bifurcated fiber optic cable to the detector elements where the narrow band pass filter passes light at wavelengths at the emission frequency of the sensor fiber assembly to the photodiodes but blocks wavelengths from the excitation light source at the excitation frequency. Therefore, the magnitude of the fluorescent emission only having been detected, the resulting photocurrent will be measured by the microprocessor to detect the target molecule with the intensity of the resulting detected fluorescence being indicative of the concentration of the target molecule. The control electronics and microprocessor precisely control the excitation current, and measures the detected signal from each narrow band pass filter and photodiode.

The computer and its display receives the measured detector current level for each sensor fiber assembly and generates an image of the target molecule source that can be used to identify the source even when low contamination of the same material is present. Furthermore, by adjusting the processing algorithm, the detector adjusts for long term exposure to a target molecule background by displaying incremental readings for each channel.

The instrument can be used to detect multiple targets by varying the fiber optic cable MIP coating material. Where mere detection of the presence of a target material is satisfactory, the sensor fiber array can be reduced to a single sensor fiber assembly for each target. The detector can be modified to detect other (non-explosive) materials by changing the MIP coating and selecting appropriate light sources, photodetectors, and filters. The detector can also be drastically reduced in size and weight through miniaturization of its components.

We claim:

1. A detector comprising:
    a fiber optic cable coated with a molecularly imprinted polymer (MIP) for binding a target molecule;
    an excitation light source connected to the fiber optic cable for causing the target molecule to fluoresce;
    a detector element connected to the fiber optic cable to detect the fluorescence; and
    a means for heating the MIP coated fiber optic cable to release the bound target molecule.

2. The detector as recited in claim 1, further comprising a fan for drawing an airflow over the coated fiber optic cable.

3. The detector as recited in claim 2 further comprising a nozzle for adjusting airflow over the coated fiber optic cable.

4. The detector as recited in claim 1, further comprising control electronics for energizing the excitation light source.

5. The detector as recited in claim 4, further comprising a microprocessor for controlling the control electronics.

6. The detector as recited in claim 1, wherein the fiber optic cable is bifurcated to permit the simultaneous transmission of light from the excitation source and fluorescence from the target molecule.

7. The detector as recited in claim 1, wherein the detector element comprises a photodiode.

8. The detector as recited in claim 7, wherein the detector element further comprises a narrow band pass filter.

9. The detector as recited in claim 1, wherein the excitation light source is a laser.

10. The detector as recited in claim 1, further comprising a computer with a display.

11. The detector as recited in claim 1, wherein the MIP will bind a target molecule from an explosive material.

12. The detector as recited in claim 1, further comprising an array of MIP coated fiber optic cables wherein each fiber optic cable in the array has a dedicated excitation light source and a dedicated detector element.

13. The detector as recited in claim 1, wherein the detector processes data from target molecules incrementally from sample to sample, thereby reducing detector susceptibility to background target molecules.

14. The detector as recited in claim 12, wherein different fiber optic cables are coated with different MIPs to permit the detection of different target molecules simultaneously.

15. The detector as recited in claim 14, wherein the MIPs will bind target molecules from a plurality of explosive materials.

16. A method for detecting a target molecule comprising the steps of:
    coating a fiber optic cable with a molecularly imprinted polymer (MIP) to bind the target molecule;
    exciting the bound target molecule with light from an excitation source to cause the target molecule to fluoresce;
    detecting the fluorescence to determine the concentration of the target molecule; and
    heating the MIP coated fiber optic cable to release the bound target molecule after the fluorescence is detected.

17. The method as recited in claim 16, further comprising the step of drawing a calibrated airflow over the MIP coated fiber optic cable.

18. The method as recited in claim 16, wherein the fiber optic cable is bifurcated to permit the simultaneous transmission of light from the excitation source and fluorescence from the target molecules.

* * * * *

UNITED STATES PATENT AND TRADEMARK OFFICE
CERTIFICATE OF CORRECTION

PATENT NO. : 6,967,103 B2
DATED : November 22, 2005
INVENTOR(S) : Schwartz et al.

It is certified that error appears in the above-identified patent and that said Letters Patent is hereby corrected as shown below:

<u>Title page,</u>
Item [75], Inventors, delete "Scott" and insert -- Stott --.

Signed and Sealed this

Seventh Day of March, 2006

JON W. DUDAS
*Director of the United States Patent and Trademark Office*